(12) United States Patent
Bacon (10) Patent No.: US 7,814,900 B2
(45) Date of Patent: Oct. 19, 2010

(54) CAN FIXTURE

(75) Inventor: Raymond John Bacon, Petersfield (GB)

(73) Assignee: Clinical Designs Limited, The Dower House, Aldsworth, Emsworth Hampshire (GB)

(*) Notice: Subject to any disclaimer, the term of this patent is extended or adjusted under 35 U.S.C. 154(b) by 730 days.

(21) Appl. No.: 10/508,688

(22) PCT Filed: Mar. 17, 2003

(86) PCT No.: PCT/GB03/01102
§ 371 (c)(1),
(2), (4) Date: Jun. 23, 2005

(87) PCT Pub. No.: WO03/080161
PCT Pub. Date: Oct. 2, 2003

(65) Prior Publication Data
US 2007/0163576 A1    Jul. 19, 2007

(30) Foreign Application Priority Data
Mar. 22, 2002 (GB) ................................. 0206811.2
Nov. 26, 2002 (GB) ................................. 0227489.2

(51) Int. Cl.
A61M 15/00 (2006.01)
A61M 16/00 (2006.01)
(52) U.S. Cl. .................... 128/200.14; 128/200.12; 128/200.21; 128/200.23; 128/203.12; 128/913; 222/402.1; 222/402.2; 206/446; 206/459.5; 206/38; 206/460; 206/497; 156/73.1
(58) Field of Classification Search ........... 128/200.11, 128/200.12, 200.14, 200.17, 200.21, 200.23, 128/203.12, 203.15, 913, 200.18, DIG. 18; 222/401.2, 402.2; 206/446, 459.5, 38, 460, 206/497; 156/73.1, DIG. 8, DIG. 9, DIG. 15
See application file for complete search history.

(56) References Cited

U.S. PATENT DOCUMENTS 2,002,835 A    5/1935  Rose (Continued)

FOREIGN PATENT DOCUMENTS

AU    776816    7/2002

(Continued)

*Primary Examiner*—Justine R Yu
*Assistant Examiner*—Clinton Ostrup
(74) *Attorney, Agent, or Firm*—Alfred A. Fressola; Ware, Fressola, Van Der Sluys & Adolphson LLP (57) ABSTRACT

A dispenser (1) comprises a can (2) and body (3). The can is an aluminum extrusion with a valve crimped into its mouth, the valve having an outlet spout (4). The crimped region (5) of the can surrounding the valve has a lesser diameter than the can has through the main part (6) of its length. The body has a mouthpiece (11) with a pivotal cover (12) drivingly connected to a cam (13). This bears on the underside of junction member (14), into a socket (15) of which the spout 4 fits. A breath actuated dose release mechanism (16) is provided. The body has a tubular section (7) for receiving the necked down region (5) of the can. A printed paper label (21) is wrapped around the joint between the body and the can to unite the can to the body in position such that when the cover is opened, a dose is dispensed by the cam (13) lifting the junction member and depressing the spout.

32 Claims, 9 Drawing Sheets

U.S. PATENT DOCUMENTS

| | | |
|---|---|---|
| 2,716,013 A | 8/1955 | Tinker |
| 2,771,631 A | 12/1956 | Bryant |
| 2,773,631 A | 12/1956 | Bryant |
| 2,922,613 A | 1/1960 | Beacham et al. |
| 2,974,835 A | 3/1961 | Herbrick |
| 3,012,454 A | 12/1961 | Brodbeck |
| 3,103,335 A | 9/1963 | Martinez |
| 3,157,179 A | 11/1964 | Paullus et al. |
| 3,181,743 A | 5/1965 | Libit et al. |
| 3,187,748 A | 6/1965 | Mitchell et al. |
| 3,190,497 A | 6/1965 | Anthon |
| 3,294,293 A | 12/1966 | Johns |
| 3,305,144 A | 2/1967 | Beres et al. |
| 3,329,389 A | 7/1967 | Clark |
| 3,395,838 A | 8/1968 | Beres et al. |
| 3,439,846 A | 4/1969 | Evras |
| 3,456,646 A | 7/1969 | Phillips et al. |
| 3,565,070 A | 2/1971 | Hanson et al. |
| 3,605,738 A | 9/1971 | Ciranna |
| 3,636,949 A * | 1/1972 | Kropp .................. 128/200.23 |
| 3,789,843 A | 2/1974 | Armstrong et al. |
| 3,789,943 A | 2/1974 | Kampert et al. |
| 3,826,413 A | 7/1974 | Warren |
| 3,913,882 A | 10/1975 | Moulet |
| 3,926,339 A | 12/1975 | Openchowski |
| 3,926,347 A | 12/1975 | Low et al. |
| 3,927,484 A * | 12/1975 | Spiegel et al . ................. 40/307 |
| 4,085,886 A | 4/1978 | Nishioka |
| 4,109,836 A | 8/1978 | Falarde |
| 4,142,651 A | 3/1979 | Leopoldi et al. |
| 4,354,660 A | 10/1982 | Stupar et al. |
| 4,393,884 A | 7/1983 | Jacobs |
| 4,414,972 A | 11/1983 | Young et al. |
| 4,457,699 A | 7/1984 | Hattori |
| 4,570,898 A | 2/1986 | Staeubli |
| 4,576,157 A | 3/1986 | Raghuprasad |
| 4,620,670 A | 11/1986 | Hughes et al. |
| 4,648,393 A | 3/1987 | Landis et al. |
| 4,664,107 A * | 5/1987 | Wass .................... 128/200.23 |
| 4,703,761 A | 11/1987 | Rathbone et al. |
| 4,707,038 A | 11/1987 | Voegeli |
| 4,803,978 A | 2/1989 | Johnson, IV et al. |
| 4,817,822 A | 4/1989 | Rand et al. |
| 4,819,834 A | 4/1989 | Thiel |
| 4,863,379 A | 9/1989 | Timerdahl et al. |
| 4,955,371 A | 9/1990 | Zamba et al. |
| 4,969,578 A | 11/1990 | Gander et al. |
| 4,972,830 A | 11/1990 | Wong et al. |
| 4,984,158 A | 1/1991 | Hillsman |
| 5,020,527 A | 6/1991 | Dessertine |
| 5,031,610 A | 7/1991 | Armstrong et al. |
| 5,042,526 A | 8/1991 | Kulakoff |
| 5,042,685 A | 8/1991 | Moulding, Jr. et al. |
| 5,060,643 A | 10/1991 | Rich et al. |
| 5,069,204 A * | 12/1991 | Smith et al. ............ 128/200.23 |
| 5,113,855 A | 5/1992 | Newhouse |
| 5,119,806 A | 6/1992 | Palson et al. |
| 5,152,456 A | 10/1992 | Ross et al. |
| 5,184,761 A | 2/1993 | Lee |
| 5,193,745 A | 3/1993 | Holm |
| 5,217,004 A | 6/1993 | Blasnik et al. |
| 5,224,472 A | 7/1993 | Pesenti et al. |
| 5,239,992 A | 8/1993 | Bougamont et al. |
| 5,273,172 A | 12/1993 | Rossbach et al. |
| 5,295,479 A | 3/1994 | Lankinen |
| 5,297,542 A | 3/1994 | Bacon |
| 5,299,701 A | 4/1994 | Barker et al. |
| 5,347,998 A | 9/1994 | Hodson et al. |
| 5,370,279 A | 12/1994 | Tardif |
| 5,388,572 A | 2/1995 | Mulhauser et al. |
| 5,402,823 A | 4/1995 | Cole |
| 5,408,994 A | 4/1995 | Wass et al. |
| 5,415,161 A | 5/1995 | Ryder |
| 5,421,482 A | 6/1995 | Garby et al. |
| 5,447,150 A | 9/1995 | Bacon |
| 5,469,843 A | 11/1995 | Hodson |
| 5,487,378 A | 1/1996 | Robertson et al. |
| 5,501,375 A | 3/1996 | Nilson |
| 5,511,540 A | 4/1996 | Bryant et al. |
| 5,544,647 A | 8/1996 | Jewett et al. |
| 5,546,932 A | 8/1996 | Galli |
| 5,549,101 A | 8/1996 | Trofast et al. |
| 5,549,226 A | 8/1996 | Kopp |
| D377,215 S | 1/1997 | Rand |
| 5,611,444 A | 3/1997 | Garby et al. |
| 5,623,920 A | 4/1997 | Bryant |
| 5,645,050 A | 7/1997 | Zierenberg et al. |
| 5,655,523 A | 8/1997 | Hodson et al. |
| 5,667,142 A | 9/1997 | Newman |
| 5,692,492 A | 12/1997 | Bruna et al. |
| D389,570 S | 1/1998 | Savolainen |
| 5,707,038 A | 1/1998 | Cocatre-Zilgien |
| 5,740,793 A | 4/1998 | Hodson et al. |
| 5,772,085 A | 6/1998 | Bryant et al. |
| 5,794,612 A | 8/1998 | Wachter et al. |
| 5,809,997 A | 9/1998 | Wolf |
| 5,826,570 A | 10/1998 | Goodman et al. |
| 5,839,429 A | 11/1998 | Marnfeldt et al. |
| 5,857,275 A * | 1/1999 | Deal ........................ 40/310 |
| 5,878,917 A | 3/1999 | Reinhard et al. |
| 5,904,139 A * | 5/1999 | Hauser ................. 128/200.23 |
| 5,996,577 A | 12/1999 | Ohki et al. |
| 6,032,835 A * | 3/2000 | Burt ....................... 222/402.1 |
| 6,085,742 A | 7/2000 | Wachter et al. |
| D433,126 S | 10/2000 | McCurry |
| 6,148,815 A | 11/2000 | Wolf |
| 6,149,054 A | 11/2000 | Cirrillo et al. |
| 6,152,130 A | 11/2000 | Abrams et al. |
| 6,202,642 B1 | 3/2001 | McKinnon et al. |
| 6,205,999 B1 | 3/2001 | Ivri et al. |
| 6,234,168 B1 | 5/2001 | Bruna |
| 6,240,918 B1 | 6/2001 | Ambrosio et al. |
| 6,260,549 B1 | 7/2001 | Sosiak |
| 6,283,365 B1 | 9/2001 | Bason |
| 6,309,623 B1 * | 10/2001 | Weers et al. ................. 424/45 |
| 6,354,290 B1 * | 3/2002 | Howlett ................. 128/200.23 |
| 6,357,442 B1 | 3/2002 | Casper et al. |
| D455,208 S | 4/2002 | Bacon et al. |
| 6,397,839 B1 * | 6/2002 | Stradella ................ 128/200.23 |
| 6,405,727 B1 | 6/2002 | MacMichael et al. |
| 6,415,784 B1 | 7/2002 | Christrup et al. |
| 6,422,234 B1 | 7/2002 | Bacon |
| 6,427,683 B1 | 8/2002 | Drachmann et al. |
| 6,431,168 B1 | 8/2002 | Rand et al. |
| 6,435,372 B1 | 8/2002 | Blacker et al. |
| 6,439,227 B1 | 8/2002 | Myrman et al. |
| 6,442,234 B1 | 8/2002 | Morken et al. |
| 6,443,146 B1 | 9/2002 | Voges |
| 6,460,537 B1 | 10/2002 | Bryant et al. |
| 6,510,847 B1 * | 1/2003 | Helgesson et al. ..... 128/200.23 |
| 6,553,988 B1 | 4/2003 | Holroyd |
| 6,581,590 B1 | 6/2003 | Genova et al. |
| 6,601,582 B2 | 8/2003 | Rand et al. |
| 6,615,827 B2 | 9/2003 | Greenwood et al. |
| D480,474 S | 10/2003 | Bowman et al. |
| 6,637,432 B2 | 10/2003 | Wakefield et al. |
| 6,655,379 B2 | 12/2003 | Clark et al. |
| 6,659,307 B1 | 12/2003 | Stradella |
| 6,672,304 B1 | 1/2004 | Casper et al. |
| 6,718,972 B2 | 4/2004 | O'Leary |
| 6,752,145 B1 | 6/2004 | Bonney et al. |
| 6,755,190 B2 | 6/2004 | Rasmussen |
| 6,866,037 B1 | 3/2005 | Aslin et al. |
| 6,866,038 B2 | 3/2005 | Bacon |

| | | | | | | |
|---|---|---|---|---|---|---|
| 6,907,876 | B1 | 6/2005 | Clark et al. | FR | 2660630 | 10/1991 |
| 6,926,002 | B2 | 8/2005 | Scarrott et al. | FR | 2701653 | 8/1994 |
| D509,898 | S | 9/2005 | Bacon et al. | FR | 2 775 668 | 9/1999 |
| 7,036,505 | B2 | 5/2006 | Bacon et al. | GB | 161969 | 7/1922 |
| 7,047,964 | B2 | 5/2006 | Bacon | GB | 727195 | 3/1955 |
| 7,093,594 | B2 | 8/2006 | Harrison et al. | GB | 939324 | 10/1963 |
| 7,107,986 | B2 | 9/2006 | Rand et al. | GB | 997617 | 7/1965 |
| 7,270,124 | B2 | 9/2007 | Rasmussen | GB | 1012565 | 12/1965 |
| 7,341,057 | B2 | 3/2008 | Scarrott et al. | GB | 1269811 | 4/1972 |
| 7,387,121 | B2 | 6/2008 | Harvey | GB | 1403826 | 8/1975 |
| 7,454,267 | B2 | 11/2008 | Bonney et al. | GB | 2079183 | 1/1982 |
| 7,597,099 | B2 | 10/2009 | Jones et al. | GB | 2191032 | 12/1987 |
| 2001/0013343 | A1 | 8/2001 | Andersson | GB | 2204799 | 11/1988 |
| 2002/0000225 | A1 | 1/2002 | Schuler et al. | GB | 2233236 | 1/1991 |
| 2002/0043262 | A1 | 4/2002 | Langford et al. | GB | 2262452 | 6/1993 |
| 2002/0056449 | A1 | 5/2002 | Wakefield et al. | GB | 2263873 | 8/1993 |
| 2003/0089368 | A1 | 5/2003 | Zhao | GB | 2264238 | 8/1993 |
| 2003/0136401 | A1 | 7/2003 | Jansen et al. | GB | 2266466 | 11/1993 |
| 2003/0183226 | A1 | 10/2003 | Brand et al. | GB | 2279571 | 1/1995 |
| 2004/0025868 | A1 | 2/2004 | Bruna | GB | 2279879 | 1/1995 |
| 2004/0079361 | A1* | 4/2004 | Clayton et al. ......... 128/200.23 | GB | 2292891 | 3/1996 |
| 2004/0089299 | A1 | 5/2004 | Bonney et al. | HU | 67279 | 3/1995 |
| 2004/0134488 | A1 | 7/2004 | Davies | JP | 63251880 | 8/1988 |
| 2004/0144798 | A1 | 7/2004 | Ouyang et al. | JP | 06027550 | 4/1994 |
| 2005/0205512 | A1 | 9/2005 | Scarrott et al. | WO | WO 92/07599 | 5/1992 |
| 2006/0278225 | A1 | 12/2006 | MacMichael et al. | WO | WO 92/07600 | 5/1992 |
| 2007/0089735 | A1 | 4/2007 | Langfor et al. | WO | WO 92/09323 | 6/1992 |
| 2008/0066750 | A1 | 3/2008 | Minshull et al. | WO | WO 92/10229 | 6/1992 |
| | | | | WO | WO 93/03783 | 3/1993 |
| | FOREIGN PATENT DOCUMENTS | | | WO | WO 93/24167 | 12/1993 |
| DE | 629163 | 4/1936 | | WO | WO 94/05359 | 3/1994 |
| DE | 3324699 | 12/1984 | | WO | WO 94/19042 | 9/1994 |
| DE | 8715223 | 2/1988 | | WO | WO 95/08484 | 3/1995 |
| DE | 3734894 | 3/1992 | | WO | WO 96/39337 | 12/1996 |
| DE | 4111895 | 10/1992 | | WO | WO 98/00770 | 1/1998 |
| DE | 295 11 334 | 11/1995 | | WO | WO 98 41254 | 9/1998 |
| DE | 19745513 | 4/1999 | | WO | WO 98/041254 | 9/1998 |
| DE | 29818662 | 3/2000 | | WO | WO 98/41254 | 9/1998 |
| DE | 10061723 | 7/2002 | | WO | WO 98/52634 | 11/1998 |
| EP | 0232235 | 8/1987 | | WO | WO 99/36116 | 7/1999 |
| EP | 0312073 | 4/1989 | | WO | WO 99/64095 | 12/1999 |
| EP | 0414536 | 2/1991 | | WO | WO 00/01436 | 1/2000 |
| EP | 0428380 | 5/1991 | | WO | 01/31578 | 5/2001 |
| EP | 0448204 | 9/1991 | | WO | WO 01/32247 | 5/2001 |
| EP | 0461281 | 12/1991 | | WO | WO 01/37909 | 5/2001 |
| EP | 0501365 | 9/1992 | | WO | WO 02 11802 | 2/2002 |
| EP | 0629563 | 12/1994 | | WO | WO 02/38207 | 5/2002 |
| EP | 0684047 | 11/1995 | | WO | WO 02/43794 | 6/2002 |
| EP | 0764312 | 4/1998 | | WO | WO 02/053295 | 7/2002 |
| EP | 1104318 | 8/1999 | | WO | WO 02/058772 | 8/2002 |
| EP | 1003583 | 5/2000 | | WO | WO 02/100468 | 12/2002 |
| EP | 1 008 362 | 6/2000 | | WO | WO 03/010154 | 2/2003 |
| EP | 1008361 | 6/2000 | | WO | WO 03/012565 | 2/2003 |
| EP | 1019125 | 7/2000 | | WO | WO 03/080161 | 10/2003 |
| EP | 0883415 | 5/2002 | | WO | WO 03/086518 | 10/2003 |
| EP | 1229953 | 8/2002 | | WO | WO 2004/001664 | 12/2003 |
| EP | 1254678 | 11/2002 | | WO | WO 2004/022142 | 3/2004 |
| FR | 2004766 | 5/1974 | | WO | WO 2004/022143 | 3/2004 |
| FR | 2471535 | 6/1981 | | WO | WO 2004/022242 | 3/2004 |
| FR | 2483262 | 12/1981 | | | | |
| FR | 2654627 | 5/1991 | | * cited by examiner | | |

CAN FIXTURE

CROSS REFERENCE TO RELATED APPLICATIONS

This application is for entry into the U.S. national phase under §371 for International Application No. PCT/GB03/01102 having an international filing date of Mar. 17, 2003, and from which priority is claimed under all applicable sections of Title 35 of the United States Code including, but not limited to, Sections 120, 363 and 365(c), and which in turn claims priority under 35 USC §119 to Great Britain Patent Application Nos. 0206811.2 and 0227489.2 filed on Mar. 22, 2002 and Nov. 26, 2002, respectively.

TECHNICAL FIELD

The present invention relates to a source fixture particularly, though not exclusively, for a source of a metered dose in a dispenser of aerosol or powder borne medicaments.

BACKGROUND OF THE INVENTION

Dispensers for inhalation of a metered dose of a medicament are widely used. In simple form, they comprise a body having a mouthpiece and an aerosol can. The can is connected to the body via its spout, which engages in a junction in the body leading to a nozzle opening towards the mouthpiece. Depression of the can towards the body dispenses the dose.

In a breath actuated dispenser, such as described as the second embodiment in our International Application No. PCT/GB01/03313, dated 24 Jul. 2001, the can is fixed to the body and a slidable junction member receives the can spout. A cam mechanism displaces the junction member—and the spout—towards the can, dispensing the dose into the breath actuatable mechanism. In that application, we envisaged locating the can by detents engageable in a groove formed around the can, at which a can closure is crimped onto the can proper. However, we have noticed that appreciable differences can exist between the depressed position of the distal end of the spout and the groove portion at which the detents engage due to the build up of tolerances. The problem is exacerbated by the detents and the groove engaging at oblique surfaces, whereby radial tolerances can influence longitudinal position. The result is that the can is insufficiently accurately located longitudinally with respect to the body and the cam mechanism.

SUMMARY OF THE INVENTION

The object of the present invention is to provide a more satisfactory fixture of the can to the body.

According to the invention there is provided a dispenser for a gaseous, gas borne or droplet substance contained in a source thereof, the dispenser comprising:

- a substance source having:
  - an external surface devoid of any feature intended for longitudinal location of the source and
  - a spout displaceable inwards of the source to a dispense position for dispensing a substance dose from the source;
- a body having:
  - a mouthpiece via which the substance dose can be inhaled and
  - a socket sized for lateral location of the source via its external surface, but devoid of any body feature intended for longitudinal location thereof;

- a junction member for the spout, the junction member being arranged in the body to be slidable to a set position for displacing the spout to its dispense position;
- an action for slidably moving the junction member to the set position; and
- a unification of the source or a source locator to the body for locating the source longitudinally with the spout in its dispense position when the junction member is in its set position, the locator where provided extending from the body, outside the source and at least partially across the end of the source to provide a longitudinal location for the source, locating it when the movable junction member acts to depress the spout inwards of the source.

According to another aspect of the invention there is provided a method in the production of a dispenser of the first aspect of the invention, the method consisting in the steps of:

- arranging the junction member in the body at its set;
- longitudinally assembling the source to the body, with the spout engaged with the junction member;
- temporarily holding the body and the source in a unification position with the spout in its dispense position and the junction member still in its set position; and
- unifying the body and the source together to fix them in their unified position.

Normally the dispenser will include a breath actuation mechanism for releasing the junction member from its set position, whereby the dose is released to the patient and the spout returns from its dispense position to its normal position. With such a dispenser, the unification step can be followed by a simulated breath actuation. Alternatively, where the action for sliding the junction member to its set position may be adapted to actuate the mechanism in the absence of a simulated breath to return the spout and the junction member to their normal positions.

The unification can be of adhesive between the source and the body, normally in the socket of the body. The body and/or the source or the locator can have a re-entrant feature and the body or the locator can have an aperture communicating with the re-entrant feature through which the adhesive was injected. The re-entrant feature can be an internal groove in the body or the locator for receiving the adhesive for a bond with the source or the body respectively. Alternatively or additionally, the re-entrant feature can be an external groove in the source at a crimp for retaining the spout and the source proper. The injected adhesive can be low temperature hot melt adhesive or fast setting two part adhesive. In either case, the adhesive will set on injection.

Alternatively the unification can be a weld between the source and the body or between the source locator and the body, the welding being performed preferably by ultrasonics or by laser.

A further alternative is a membrane such as a wrapping or a printed label around both the source and the body and unified to both. This alternative can be additional to the use of an adhesive or a weld.

Whilst it is envisaged that the membrane may be of paper, it equally may be of plastics material.

The membrane may be circumferentially continuous around the body as in a shrink wrapping, or it may discontinuous, as in a label wrapped largely around them. It is also conceivable that two or more separate membranes could be used, one to one side and the other to the other side.

The membrane may have self-adhesive applied to it or adhesive may be applied directly to the source and the body. Indeed the membrane can be of material which is self-adhesive.

Where the label is a continuous tube, it can be applied as a shrink wrapping. This is particularly advantageous where the body and the source are of different diameters. A shrink wrapping may grip the body and the source sufficiently tightly to unify them together without requiring adhesive. Alternatively, this may applied for instance as hot melt. The body and/or the source may be contoured to enhance the grip of the shrink wrapping on them. Such contouring may be used for adhesive labels.

Again, it is envisaged that the membrane may be welded, as by ultra-sonic welding to either or both of the source and the body. Whilst the latter is currently of plastics material, the former is likely to be of plastics material in due course, facilitating welding. Ultrasonic welding is possible even where the source is of metal or indeed of glass provided they are coated with plastics material or indeed even if they are not, provided that the welding causes the melted body material to adhere to the source—when cooled again—sufficiently for no relative movement between them under normal use conditions.

More specifically, the following weldings can be envisaged:

i. Where the source is essentially of plastics material or at least has a plastics material portion, such as its main containing portion, engageable with the body, the two can be ultrasonically welded together.

ii. Similarly, where the source has a glass container, typically with a valve connected to it by a crimped ferrule, and the glass is covered with a plastics material, either as a shrink wrapping or a spray coating or insert moulding or co-moulding, and the glass container fits closely within the body, the two can be ultrasonically welded together.

iii. Again, where the source is metallic, either of plastics material coated metal or with sprayed on plastics material, the source can be welded to the body where the two engage with each other. This is possible either as regards a main container of the source or a crimped on ferrule.

In accordance with particular feature of the invention, the source and the body are relatively located in the temporary holding step by:

urging the source towards the junction member with a force sufficient to depress the spout towards the source proper and dispense a dose of the substance to the junction member.

BRIEF DESCRIPTION OF THE DRAWINGS

To help understanding of the invention, specific embodiments thereof will now be described by way of example and with reference to the accompanying drawings, in which.

DETAILED DESCRIPTION

Figure 1:
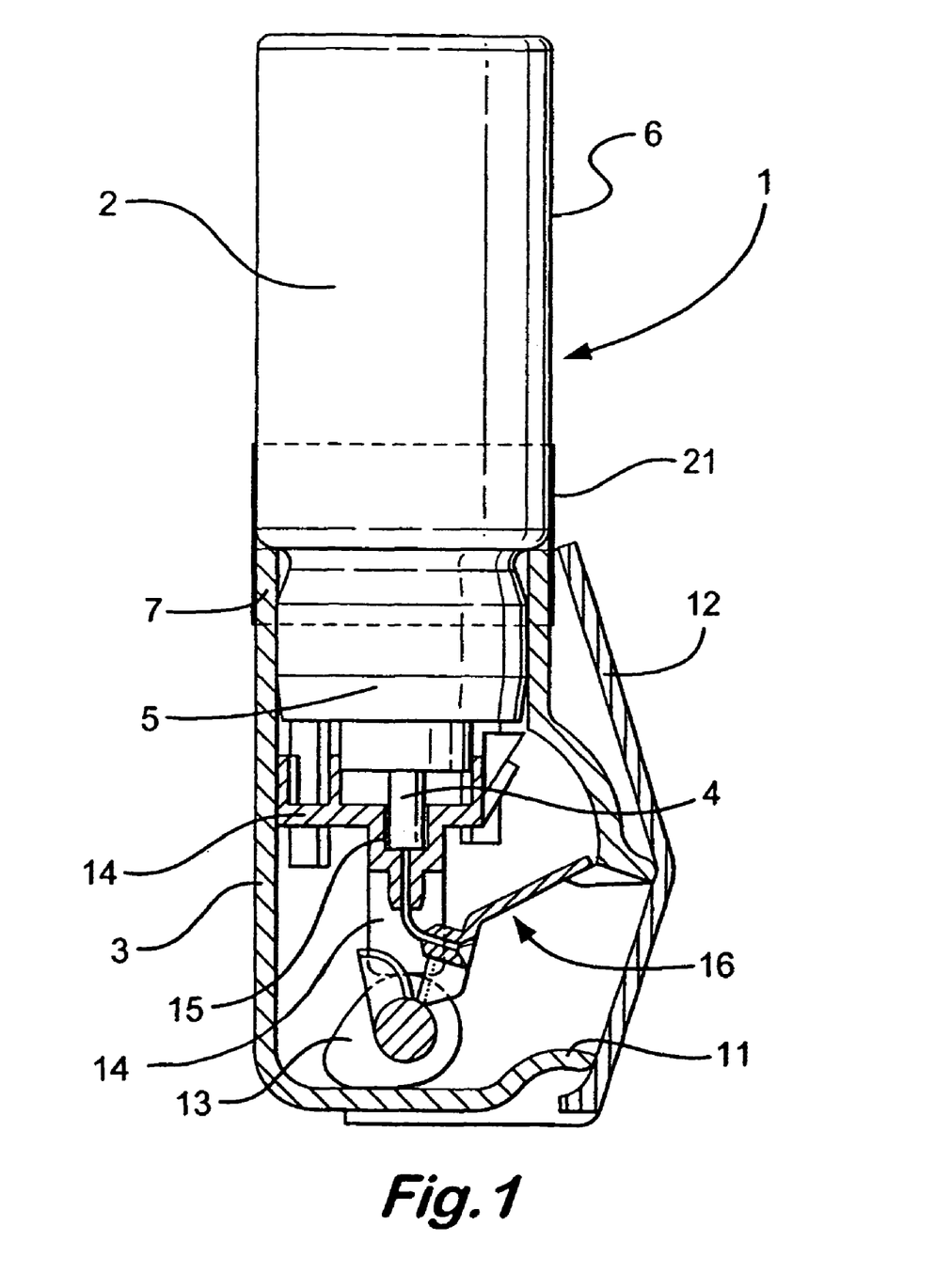
FIG. 1 is a cross-sectional side view of a dispenser of the invention, shown in a closed position.
Figure 2:
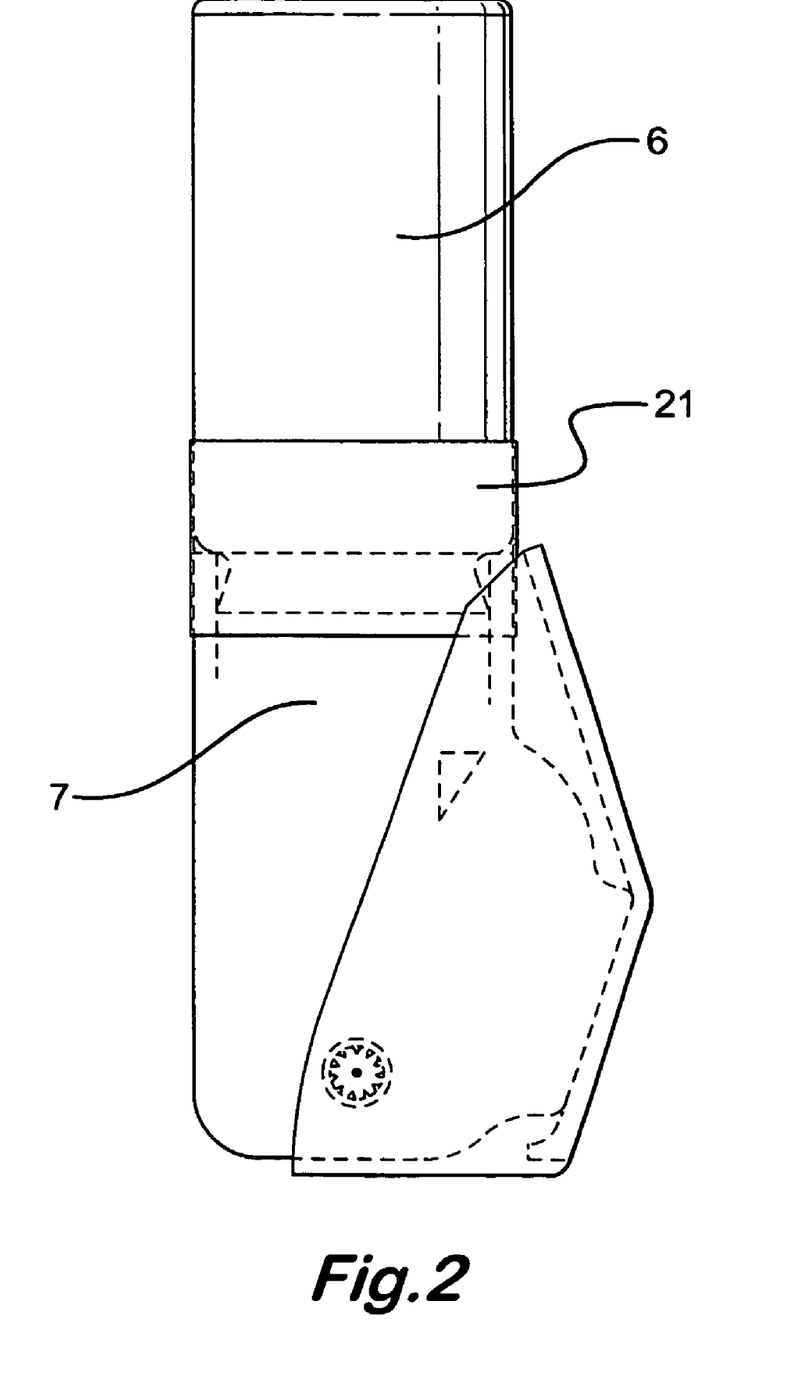
FIG. 2 is a similar ordinary side view.

Referring first to FIGS. 1 & 2 of the drawings, a dispenser 1 comprises a can 2 and a body 3. The can is an aluminium extrusion with a valve crimped into its mouth, the valve having an outlet spout 4. The crimped region 5 of the can surrounding the valve has a lesser diameter than the can has through the main part 6 of its length.

The body has a mouthpiece 11 with a pivotal cover 12 drivingly connected to a cam 13. This bears on the underside of a junction member 14, into a socket 15 of which the spout 4 fits. A breath actuated dose release mechanism 16 is provided. Its details form no part of the present invention. The reader is referred our International Application mentioned at the beginning of this specification for details of this mechanism.

The body has a tubular section 7 for receiving the necked down region 5 of the can. The tubular section and the main part of the can having the same external diameter.

A printed paper label 21 coated with self-adhesive is wrapped around the joint between the body and the can to unite the can to the body in position such that when the cover is opened, a dose is dispensed by the cam 13 lifting the junction member and depressing the spout. The dose is retained since the action of opening of the cover sets the breath actuation mechanism. On breathing in through the mouthpiece by the user, the mechanism releases the dose for inhalation.

Figure 3:
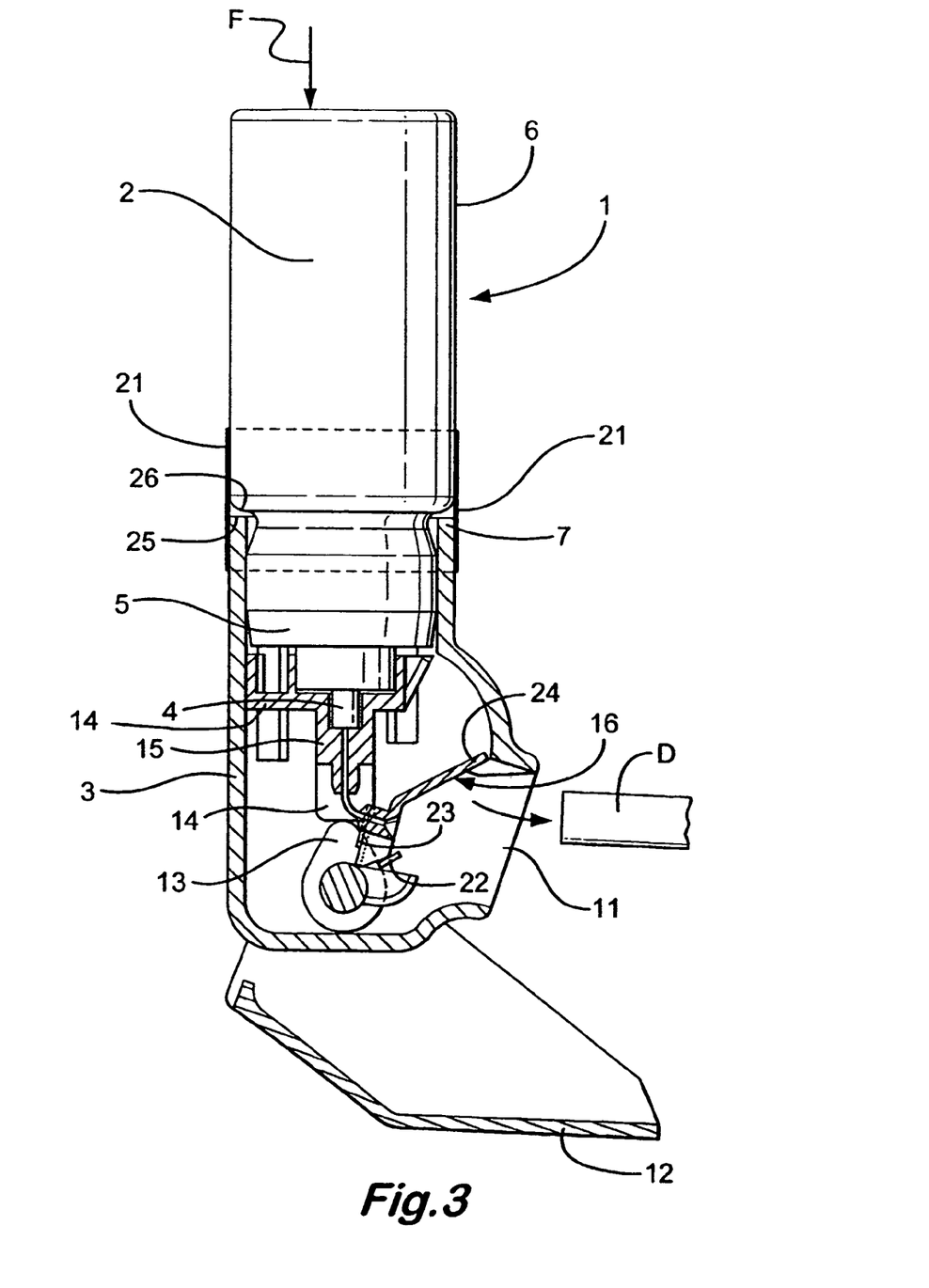
FIG. 3 is a view similar to FIG. 1 of the dispenser during unification of its can to its body.

In order to establish correct positioning of the can with respect to the body, prior to positioning of the label, during assembly of the dispenser, the pre-assembled body 3, cover 12, junction member 14 and release mechanism 16 are set to their "cover open" position as shown in FIG. 3, i.e. with the cover pivoted down from the FIG. 1 position. When the dispenser comes to be used, the FIG. 3 position is one in which with the can united to the body, the release mechanism is lifted to move the spout 4 inwards of the can, i.e. the spout is depressed. With the mentioned components set to their "cover open" position a can is introduced into the tubular section of the body. With the can and body properly aligned, the spout engages in the socket 15 in the junction member. A predetermined force F is applied to ensure that the spout is fully depressed. This causes the can to release into the release mechanism a dose, which will usually be a metered dose. Thus in this position of the can in the body, when the cover is opened in use, another dose will be released. With the force still applied the label is applied to the can and the body fixing their relative position.

The label can pass fully around the can or merely pass most of the way around.

Once the can and the body are united by the label, air can be drawn into a duct D close to the mouthpiece to induce the release mechanism to release the dose. The cover can then be closed and the dispenser is ready for shipping and use. Alternatively, the cover can be closed without induced release. The closure causes a finger 22 fast with the cam to engage with a finger 23 fast with the flap 24 of the release mechanism whereby the flap is moved to its FIG. 1 position and the dose is released.

It should be noted that whereas a superficial inspection of FIGS. 1 and 3 might suggest that the can is located by abutment between the end 25 of the tubular section of the body and the step 26 in the can, there is clearance between these features when the can is pushed in to its position in which spout is depressed and the release mechanism is set.

Figure 4:
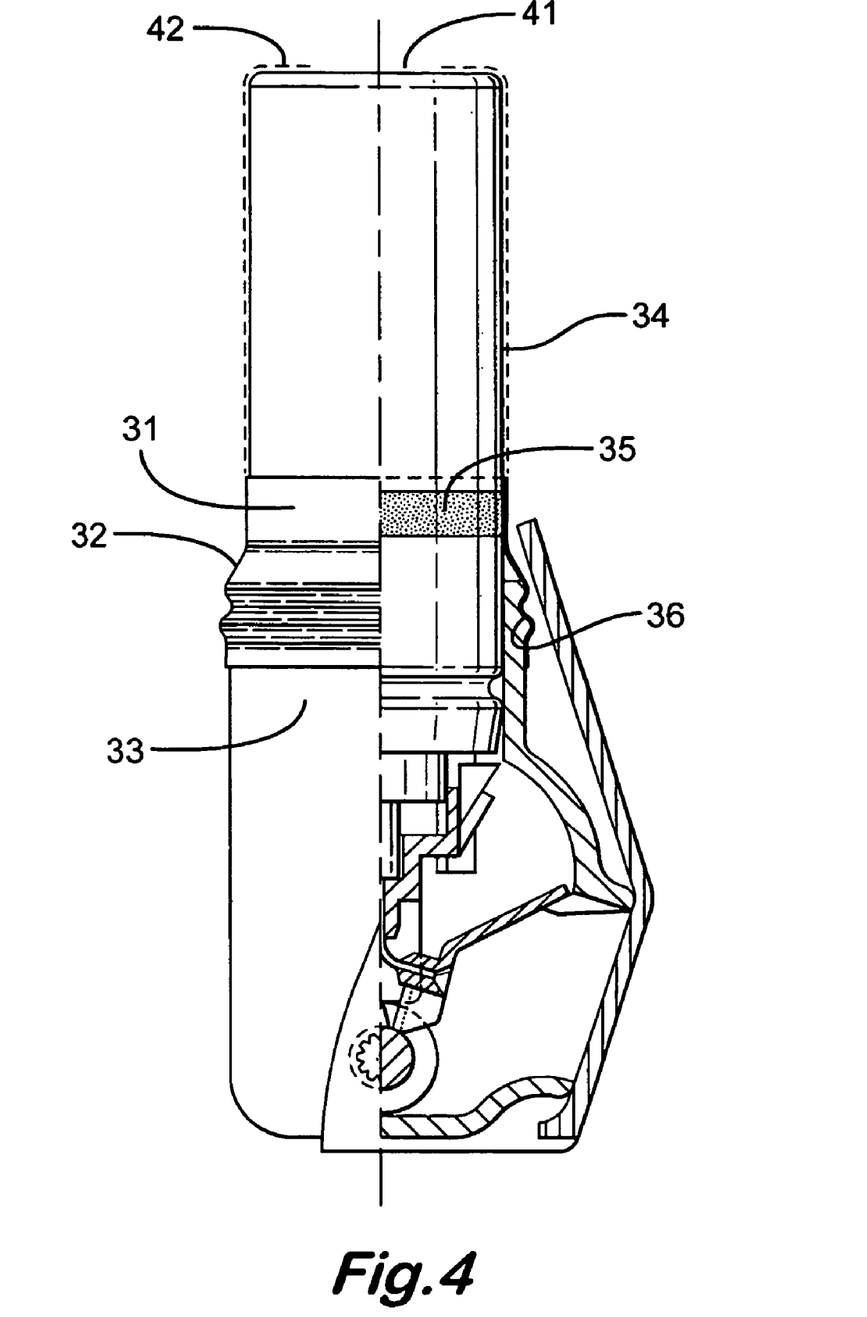
FIG. 4 is a similar view partially in cross-section of a variant of the dispenser

Alternatively the label can be a shrink wrap label 31, as shown in FIG. 4. This is of particular advantage where the body stands slightly proud of the can, as shown in FIG. 3, in that a tapered portion 32 of the label bridges the change in diameter from the larger diameter tubular section 33 to the smaller diameter can 34. The tapered portion acts in tension in use of the device. To enhance grip of the shrink wrap, the can and body can be provided with adhesive 35 and/or surface formations 36.

Figure 5:
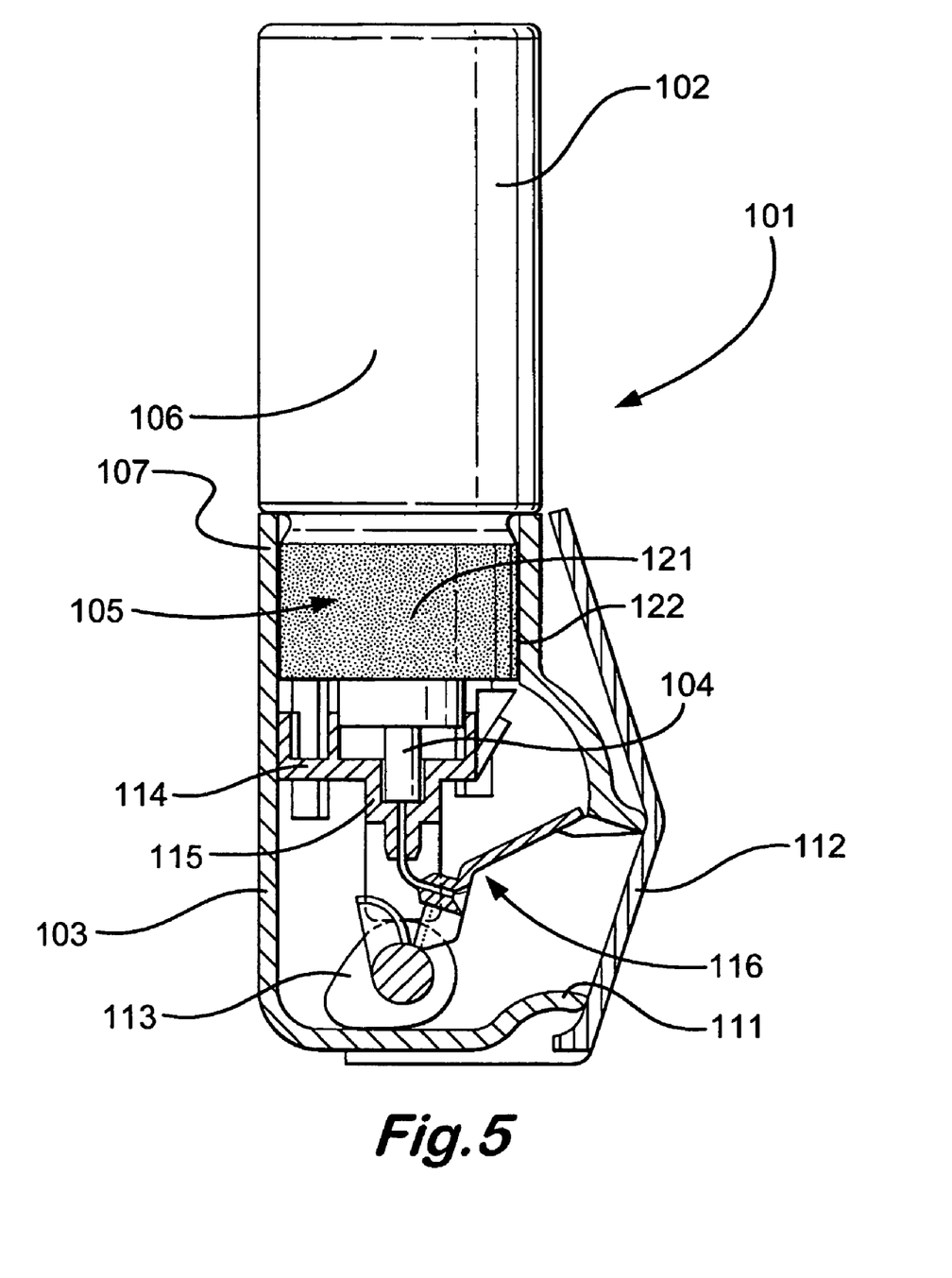
FIG. 5 is a cross-sectional side view of another dispenser of the present invention, shown in a closed position.

Referring to FIG. 5 of the drawings, the dispenser 101 thereshown comprises a can 102 and a body 103. As with the dispenser of FIG. 1, the can is an aluminium extrusion with a valve crimped into its mouth, the valve having an outlet spout 104. The crimped ferrule 105 connecting the valve to the main part 106 of the can has a lesser diameter than the can has through the main part of its length.

The body has a mouthpiece 111 with a pivotal cover 112 drivingly connected to a cam 113. This bears on the underside of a junction member 114, into a socket 115 of which the spout 104 fits. A breath actuated dose release mechanism 116 is provided. The body has a tubular section 107 for receiving the ferrule 105 of the can. The tubular section and the main part of the can having the same external diameter.

The ferrule is made of aluminium with a coating 121 of polypropylene of sufficient thickness that it can be ultrasonically welded 122 to the tubular section 107 of the body. The can is welded into the body in such position that when the cover is opened, a dose is dispensed by the cam 113 lifting the junction member and depressing the spout. The dose is retained since the action of opening of the cover sets the breath actuation mechanism. On breathing in through the mouthpiece by the user, the mechanism releases the dose for inhalation.

In order to establish the correct positioning prior to welding, during assembly of the dispenser, the pre-assembled body 103, cover 112, junction member 114 and release mechanism 116 are set to their "cover open" position, i.e. with the cover pivoted down from the FIG. 5 position, in which in the presence of the can the release mechanism is lifted to depress the spout 104. The can is introduced into the tubular section of the body. With the can and body properly aligned, the spout engages in the socket 115 in the junction member. A predetermined force is applied to ensure that the spout is fully depressed. This causes the can to release into the release mechanism a dose, which will usually be a metered dose. Thus in this position of the can in the body, when the cover is opened in use, another dose will be released. With the force still applied the can is ultrasonically welded in position.

Figure 6:
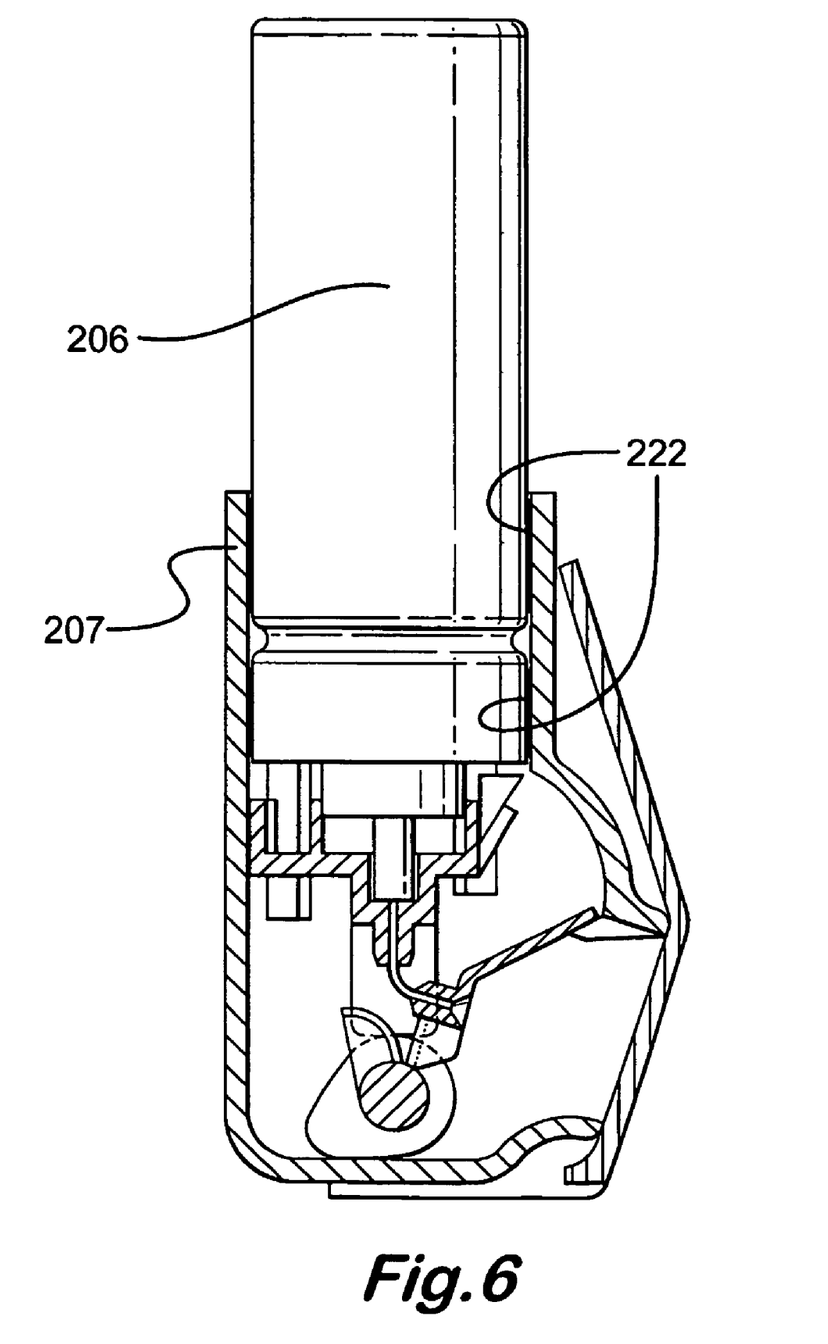
FIG. 6 is a similar view of a further dispenser of the invention.

FIG. 6 shows an alternative, in which the tubular body section 207 is longer and the can proper 206 has the same diameter as the ferrule 205. Both the ferrule and the can are spray coated with polypropylene whereby a weld 222 can be established with the section 207, both at the ferrule and the portion of the can within the tublar body section.

Figure 7:
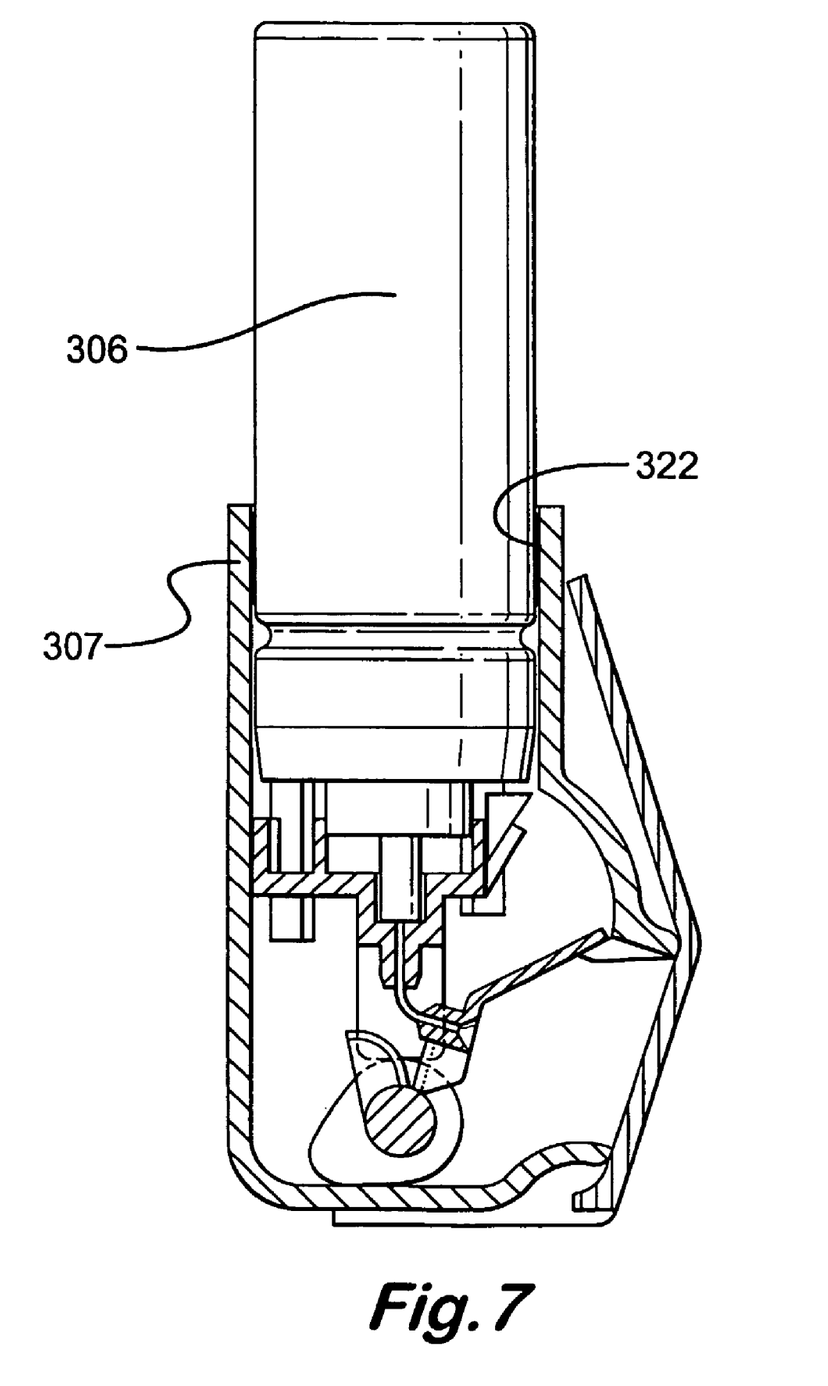
FIG. 7 is a similar view of yet another dispenser of the invention.

FIG. 7 yet another alternative where the "can" proper 306 is of glass and spray coated with polypropylene. This is welded 322 to the body section 307 surrounding it.

Figure 8:
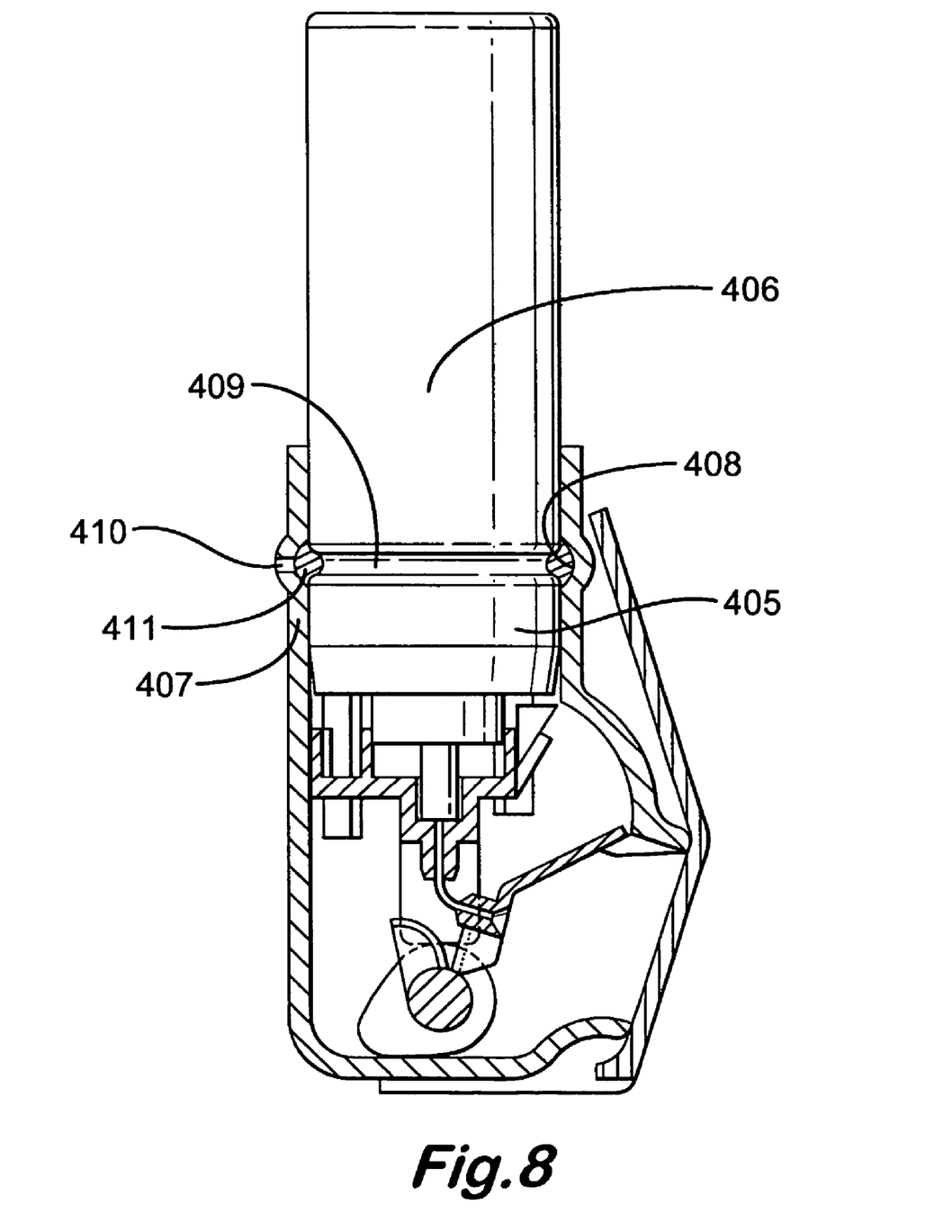
FIG. 8 is a similar view of yet a further dispenser of the invention.

FIG. 8 shows another glued dispenser. It has an aperture 410 in its tubular section 407, through which low temperature hot melt adhesive or fast curing two-part adhesive can be injected to set in the groove 409 between the crimped portion 405 of the can and the main body portion 406. A further groove 408 can be provided in the tubular section, to provide a larger cross-sectional area flow path for the adhesive and also to provide a re-entrant key in both the body and the source for the adhesive, whereby the adhesive 411 locates the source in the body not only by its adhesive nature, but also as a solid block keying into both the features. It can also be envisaged that, where the source has little or no groove at the joint between the crimped on valve for the spout and the can proper, the re-entrant groove in the tubular section 407 may be relied on alone to provide the flow passage for the adhesive.

Figure 9:
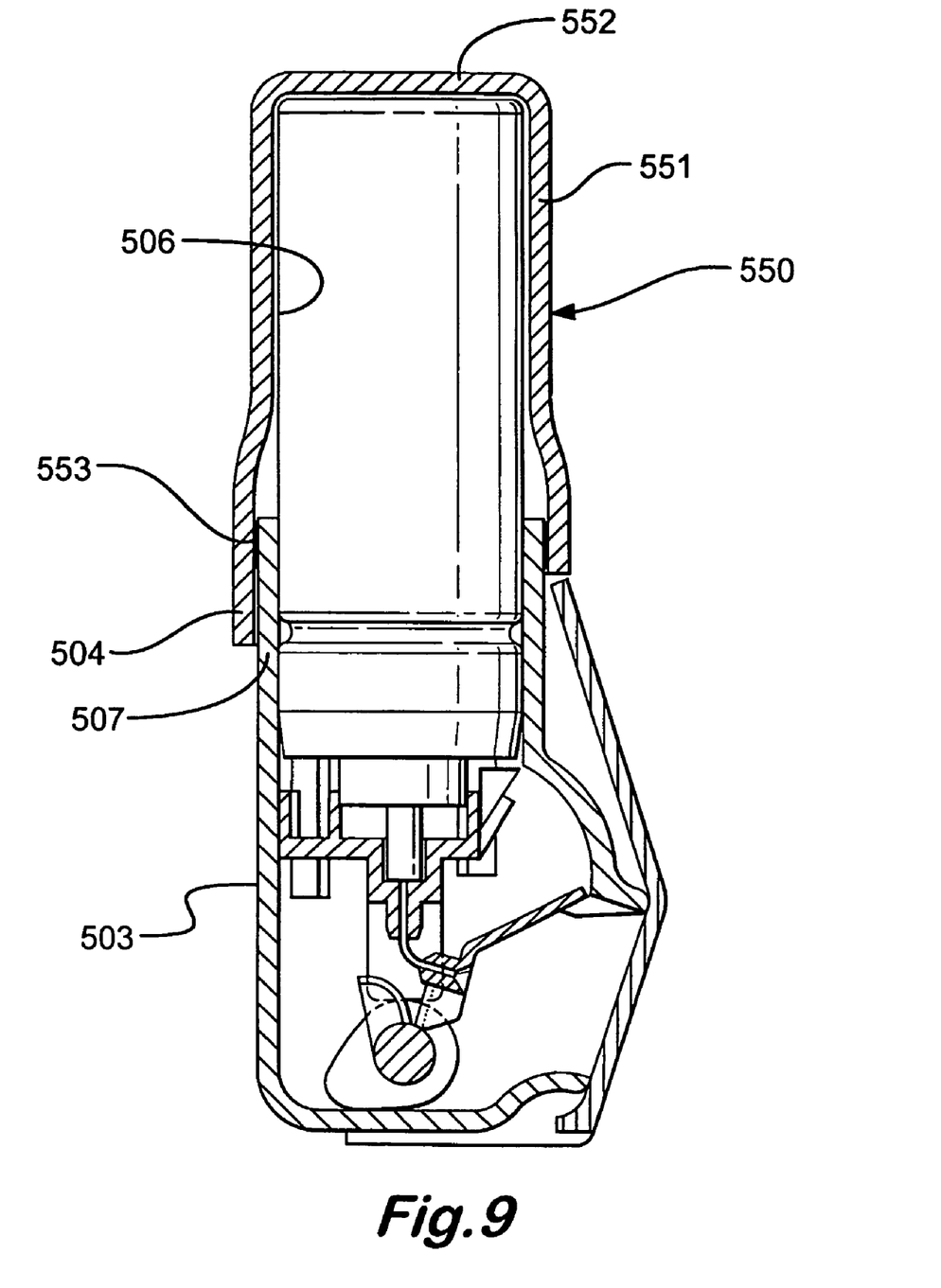
FIG. 9 is a similar view of the last described dispenser of the invention.

FIG. 9 shows a further dispenser of the invention, with a source locator 550. It is a plastics injection moulding. It surrounds the can 506 with a generally cylindrical sleeve 551 along the length of the can extending from the tubular section 507 of the body 503. The sleeve of the locator has an in-turned closure 552 at its end remote from the body 503. The can is a loose fit within the locator sleeve, which allows positioning force F on the sleeve to be conveyed to the can of the source for its correct positioning. The polymers of the locator and of the body are chosen whereby the sleeve is transparent to laser irradiation, whilst the body absorbs the radiation, thus melting and forming a weld 553 with the locator, at their overlap 504 when the parts are properly located and irradiated for locating the can and the body.

The invention is not intended to be restricted to the details of the above described embodiment. For instance, the weld can be replaced by adhesive. Further the embodiment of FIG. 4 can be varied with the shrink wrapping extending along the full length of the source—shown in dashed lines in FIG. 4—and just over its end 41. Thus the shrink wrapping holds the can not only by friction along its length but by physical location where it forms a rim 42 at the end of the can.

The invention claimed is:

1. A dispenser for a gaseous, gas borne or droplet substance contained in a can thereof, the dispenser comprising:
   a can containing said substance having:
      a spout displaceable inwards of the can to a dispense position for dispensing a substance dose from the can;
   a body having:
      a mouthpiece via which the substance dose can be inhaled and
      a socket sized for lateral location of the can via its external surface, but devoid of any body feature intended for longitudinal location thereof;
   a junction member for the spout, the junction member being arranged in the body to be slidable to a set position for displacing the spout to its dispense position;
   a mechanism for slidably moving the junction member to the set position; and
   a unification of the can to the body which locates the can longitudinally with the spout in its dispense position when the junction member is in its set position, or a unification of a can locator to the body which locates the can longitudinally with the spout in its dispense position when the junction member is in its set position, the locator extending from the body, outside the can and at least partially across an end of the can to provide a longitudinal location for the can, locating the can when the movable junction member acts to depress the spout inwards of the can.

2. A dispenser as claimed in claim 1, including a breath actuation mechanism for releasing the junction member from its set position, whereby the dose is released to the patient and the spout returns from its dispense position to its normal position.

3. A dispenser as claimed in claim 1, wherein the mechanism for sliding the junction member to its set position is adapted to actuate the mechanism in the absence of a simulated breath to return the spout and the junction member to their normal positions.

4. A dispenser as claimed in claim 1, wherein the unification is of adhesive between the can or the locator and the body.

5. A dispenser as claimed in claim 4, wherein the adhesive is in the socket of the body.

6. A dispenser as claimed in claim 4, wherein the body and/or the can or the locator have a re-entrant feature and the body or the locator has an aperture communicating with the re-entrant feature through which the adhesive was injected.

7. A dispenser as claimed in claim 6, wherein the re-entrant feature is an internal groove in the body or the locator for receiving the adhesive for a bond with the can or the body respectively.

8. A dispenser as claimed in claim 6, wherein the re-entrant feature is an external groove in the can at a crimp for retaining the spout and the can proper.

9. A dispenser as claimed in claim 1, wherein the unification is a weld between the can or the locator and the body.

10. A dispenser as claimed in claim 9, wherein weld is an ultrasonic weld or a laser weld.

11. A dispenser as claimed in claim 9, wherein the can and/or the locator and the body are of plastics material.

12. A dispenser as claimed in claim 9, wherein the can is of glass or metal and is coated with plastics material.

13. A dispenser as claimed in claim 9, wherein the can is of un-coated glass or metal.

14. A dispenser as claimed in claim 9, wherein the weld is between a container of the can and the body.

15. A dispenser as claimed in claim 9, wherein the weld is between a ferrule of the can and the body.

16. A dispenser as claimed in claim 9, wherein the weld is between can locator and the body.

17. A dispenser as claimed in claim 1, wherein the unification is a membrane around both the can or the locator and the body and unified to both.

18. A dispenser as claimed in claim 17, wherein the membrane is a wrapping.

19. A dispenser as claimed in claim 17, wherein the membrane is a printed label.

20. A dispenser as claimed in claim 17, wherein the membrane is of paper.

21. A dispenser as claimed in claim 17, wherein the membrane is of plastics material.

22. A dispenser as claimed in claim 17, wherein the membrane is circumferentially continuous around the body.

23. A dispenser as claimed in claim 17, wherein the membrane is a shrink wrapping.

24. A dispenser as claimed in claim 17 wherein the membrane is discontinuous around the can or the locator and the body.

25. A dispenser as claimed in claim 24, wherein the discontinuous membrane comprises two or more separate membrane portions could be used, one to one side of the can or the locator and the body and the other to the other side.

26. A dispenser as claimed in claim 17, wherein the membrane has self-adhesive applied to it.

27. A dispenser as claimed in claim 17, wherein the membrane is of self adhesive material.

28. A dispenser as claimed in claim 17, wherein adhesive for the membrane is applied directly to the can or the locator and the body.

29. A dispenser as claimed in claim 17, wherein the can or the locator and/or the body are contoured to enhance the grip of the membrane to them.

30. A method in the production of a dispenser for a gaseous, gas borne or droplet substance contained in a can thereof, the dispenser comprising:
a can containing said substance having:
a spout displaceable inwards of the can to a dispense position for dispensing a substance dose from the can;
a body having:
a mouthpiece via which the substance dose can be inhaled and
a socket sized for lateral location of the can via its external surface, but devoid of any body feature intended for longitudinal location thereof;
a junction member for the spout, the junction member being arranged in the body to be slidable to a set position for displacing the spout to its dispense position;
a mechanism for slidably moving the junction member to the set position; and
a unification of the can to the body for locating the can longitudinally with the spout in its dispense position when the junction member is in its set position, or a unification of a can locator to the body for locating the can longitudinally with the spout in its dispense position when the junction member is in its set position, the locator extending from the body, outside the can and at least partially across an end of the can to provide a longitudinal location for the can, locating the can when the movable junction member acts to depress the spout inwards of the can,
the method comprising the steps of:
arranging the junction member in the body at its set position;
longitudinally assembling the can to the body, with the spout engaged with the junction member;
temporarily holding the body and the can in a unification position with the spout in its dispense position and the junction member still in its set position; and
unifying the body and the can together or unifying the body and can together via the can locator, if present, to fix the body and can in their unification position.

31. A method as claimed in claim 30, wherein the dispenser includes a breath actuation mechanism for releasing the junction member from its set position, whereby the dose is released to the patient and the spout returns from its dispense position to its normal position, the unification step being followed by a simulated breath actuation.

32. A method as claimed in claim 30, wherein the can and the body are relatively located in the temporary holding step by urging the can towards the junction member with a force sufficient to depress the spout towards the can proper and dispense a dose of the substance to the junction member.

* * * * *